United States Patent
Jianying

(10) Patent No.: US 7,636,422 B2
(45) Date of Patent: Dec. 22, 2009

(54) X-RAY CT APPARATUS AND X-RAY TUBE CURRENT DETERMINING METHOD

(75) Inventor: Li Jianying, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/342,355

(22) Filed: Dec. 23, 2008

(65) Prior Publication Data

US 2009/0168950 A1 Jul. 2, 2009

(51) Int. Cl.
*H05G 1/34* (2006.01)
(52) U.S. Cl. .............. 378/110; 378/95; 378/8
(58) Field of Classification Search ............ 378/4–20, 378/62, 95, 101, 108–112
See application file for complete search history.

(56) References Cited

U.S. PATENT DOCUMENTS

| | | | |
|---|---|---|---|
| 5,103,469 A | 4/1992 | Tanaka | 378/16 |
| 5,379,333 A | 1/1995 | Toth | 378/16 |
| 5,450,462 A | 9/1995 | Toth et al. | 378/16 |
| 5,696,807 A | 12/1997 | Hsieh | 378/109 |
| 5,822,393 A | 10/1998 | Popescu | 378/108 |
| 5,982,846 A | 11/1999 | Toth et al. | 378/19 |
| 6,198,789 B1 | 3/2001 | Dafni | 378/8 |
| 6,385,280 B1 | 5/2002 | Bittl et al. | 378/16 |
| 6,765,983 B2 | 7/2004 | Yan et al. | 378/8 |
| 7,006,593 B2 | 2/2006 | Kokubun et al. | 378/8 |
| 7,116,756 B2 * | 10/2006 | Klingenbeck-Regn et al. | 378/95 |
| 7,142,630 B2 | 11/2006 | Suzuki | 378/16 |
| 7,212,602 B2 | 5/2007 | Tsujii | 378/8 |
| 7,366,277 B2 | 4/2008 | Goto et al. | 378/4 |

FOREIGN PATENT DOCUMENTS

| | | |
|---|---|---|
| JP | 2002-330961 | 11/2002 |
| JP | 2006-116137 | 5/2006 |

* cited by examiner

*Primary Examiner*—Courtney Thomas
(74) *Attorney, Agent, or Firm*—Armstrong Teasdale LLP

(57) ABSTRACT

This invention is provided to determine a tube current at the imaging of the heart by an X-ray CT apparatus in such a manner that image noise becomes constant. Upon determining a tube current of an X-ray tube at the time that the heart is imaged by an X-ray CT apparatus, the tube current is determined based on an index related to image's noise and a BMI of a subject. The noise is at a central portion of an ascending main artery. Determining the tube current is conducted using a function with the BNI as a variable. The function is given in the form of a polynomial equation of the BMI. Each coefficient of the polynomial equation is a function of the index.

20 Claims, 4 Drawing Sheets

X-RAY CT APPARATUS AND X-RAY TUBE CURRENT DETERMINING METHOD

CROSS REFERENCE TO RELATED APPLICATIONS

This application claims the benefit of Chinese Patent Application No. 200710300497.9 filed Dec. 28, 2007, which is hereby incorporated by reference in its entirety.

BACKGROUND OF THE INVENTION

The embodiments described herein relate to an X-ray CT apparatus and an X-ray tube current determining method, and particularly to a technique for determining a tube current of an X-ray tube at the time that the heart is imaged or photographed by an X-ray CT (Computed Tomography) apparatus.

Even of X-ray CT apparatuses, one called a VCT (Volume CT), an MDCT (Multi-row Detector CT) or a multi-slice CT or the like is configured so as to detect a cone beam X-ray radiated from an X-ray tube by means of a multi-row detector having 64 rows to 256 rows.

This type of X-ray CT apparatus is used with emphasis on 3D-image photography of the heart or circulatory system by paying attention to the size of coverage in a body-axis direction and the level or degree of efficiency of a helical scan derived therefrom (refer to, for example, Japanese Unexamined Patent Publication No. 2002-330961 (paragraph numbers 0038-0042 and FIG. 14)).

When the range of a helical scan is long in the direction of a body axis as in the case where, for example, a main artery system is imaged or photographed from its main portion to its end, a tube current of an X-ray tube is dynamically adjusted according to the progress of the helical scan in such a manner that the dose of X rays is optimized even at any position on the body axis. The adjustment to the tube current is conducted based on an index of image noise (refer to, for example, Japanese Unexamined Patent Publication No. 2006-116137 (paragraph numbers 0040-0065 and FIG. 5)).

Such a tube current adjustment is also called "automA" or "smartmA". If the automA and the smartmA are taken, then the image noise becomes constant regardless of the body type or the like of a patient and image quality is stabilized.

BRIEF DESCRIPTION OF THE INVENTION

There was a case in which such a tube current adjustment as described above was unsuitable for use in cardiac imaging. That is, this is because since the size of a region to be imaged or photographed changes due to heart or cardiac motion or the like in the case of the cardiac imaging, the relation of correspondence between an index related to image noise and a tube current for attaining it is hard to be established for the cardiac imaging. Thus, since the cardiac imaging is normally conducted under a constant tube current, the image noise is affected by the body type or the like of a patient and affected even by the skill of a photographer. Therefore, the quality of an image is not stabilized and accurate X-ray interpretation is difficult.

Thus, a problem of the present invention is to realize an X-ray CT apparatus and an X-ray tube current determining method which determines a tube current at the time that the heart is imaged or photographed by the X-ray CT apparatus, in such a manner that image noise becomes constant.

In a first aspect, an X-ray CT apparatus includes an X-ray radiation/detection device having an X-ray tube, and an X-ray detector which detects X rays applied from the X-ray tube, and an X-ray tube current setting unit which sets an X-ray tube current determined based on an index related to image noise and a BMI of a subject.

In a second aspect, and according to the first aspect, the X-ray tube current setting unit sets an X-ray tube current at imaging of the heart of the subject.

In a third aspect, and according to the second aspect, wherein the noise is at a central portion of an ascending main artery.

In a fourth aspect, and according to any of the first to third aspects, the X-ray tube current is calculated using a function with the BMI as a variable.

In a fifth aspect, and according to the fourth aspect, the function is given as a polynomial equation of the BMI.

In a sixth aspect, and according to the fifth aspect, each coefficient of the polynomial equation is a function of the index.

In a seventh aspect, an X-ray CT apparatus includes an X-ray radiation/detection device having an X-ray tube, and an X-ray detector which detects X rays applied from the X-ray tube, a noise measuring unit which measures image noise obtained by preliminary imaging of a subject, which is conducted ahead of actual imaging of the subject, and an X-ray tube current setting unit which sets an X-ray tube current at the actual imaging, determined based on both an X-ray tube current at the preliminary imaging and a ratio between a measured value of noise at the preliminary imaging and each index related to image noise.

In an eighth aspect, and according to the seventh aspect, the X-ray tube current setting unit sets an X-ray tube current at imaging of the heart of the subject.

In a ninth aspect, and according to the eighth aspect, the X-ray tube current setting unit sets an X-ray tube current at execution of angiographic imaging of the heart of the subject.

In a tenth aspect, and according to the eighth aspect, the noise is at a central portion of an ascending main artery.

In an eleventh aspect, a method for setting an X-ray tube current of an X-ray CT apparatus includes setting an X-ray tube current determined based on an index related to image noise and a BMI of a subject.

In a twelfth aspect, and according to the eleventh aspect, the method further includes a step of setting an X-ray tube current at imaging of the heart of the subject.

In a thirteenth aspect, and according to the twelfth aspect, the noise is at a central portion of an ascending main artery.

In a fourteenth aspect and according to any one of the eleventh to thirteenth aspects, the X-ray tube current is calculated using a function with the BMI as a variable.

In a fifteenth aspect, and according to the fourteenth aspect, the function is given as a polynomial equation of the BMI.

In a sixteenth aspect, and according to the fifteenth aspect, each coefficient of the polynomial equation is a function of the index.

In a seventeenth aspect, a method for setting an X-ray tube current of an X-ray CT apparatus includes measuring image noise obtained by preliminary imaging of a subject, which is conducted ahead of actual imaging of the subject, and setting an X-ray tube current at the actual imaging, and determined based on both an X-ray tube current at the preliminary imaging and a ratio between a measured value of noise at the preliminary imaging and each index related to image noise.

In an eighteenth aspect, and according to the seventeenth aspect, the method further includes a step of setting an X-ray tube current at imaging of the heart of the subject.

In a nineteenth aspect, and according to the eighteenth aspect, the method further includes setting an X-ray tube current at execution of angiographic imaging of the heart of the subject.

In a twentieth aspect, and according to the eighteenth aspect, the noise is at a central portion of an ascending main artery.

Thus, an X-ray tube current is determined based on each index related to image noise and a BMI of a subject is set in a method for setting an X-ray tube current of an X-ray CT apparatus. Therefore, a tube current at the imaging of the heart by the X-ray CT apparatus can be determined such that the image noise becomes stable.

Since the noise is at a central portion of an ascending main artery, it is suitable for obtaining each noise index for cardiac imaging.

Since the determination of the tube current is performed using a function with the BMI as a variable, a tube current suitable for the constitution or body type of a patient can be obtained.

Since the function is given as a polynomial equation of the BMI, it is easy to store it in a memory.

Since each coefficient of the polynomial equation is of a function of the index, a tube current adapted to the index can be determined.

In a method for setting an X-ray tube current of an X-ray CT apparatus, image noise obtained by preliminary imaging of a subject, which is conducted ahead of actual imaging of the subject, is measured, and an X-ray tube current at the actual imaging, determined based on both an X-ray tube current at the preliminary imaging and a ratio between a measured value of noise at the preliminary imaging and each index related to image noise is set. Therefore, a tube current at the time that the heart is imaged by the X-ray CT apparatus can be determined in such a manner that the image noise becomes stable.

Since the imaging corresponds to angiographic imaging, a coronary image can be obtained.

Since the noise is at a central portion of an ascending main artery, it is suitable for obtaining each noise index for cardiac imaging.

DETAILED DESCRIPTION OF THE INVENTION

Figure 1:
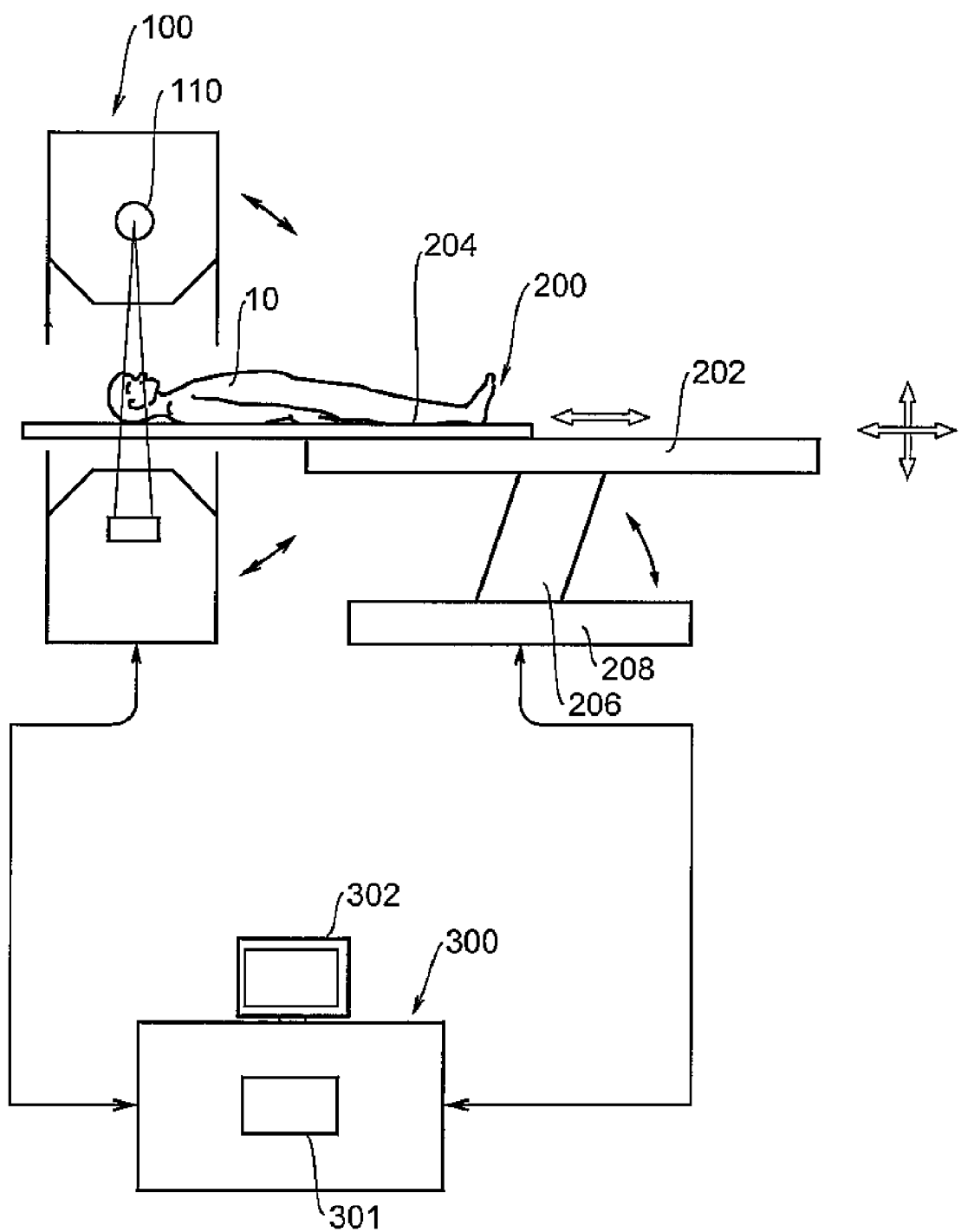
FIG. 1 is a diagram showing a construction of an X-ray CT apparatus which makes use of a tube current determining method corresponding to one example of a best mode for carrying out the invention.

Embodiments of the invention will hereinafter be described with reference to the accompanying drawings. Incidentally, the present invention is not limited to the embodiments described herein. A typical construction of an X-ray CT apparatus is shown in FIG. 1. A tube current determining method illustrative of one embodiment is utilized in the present apparatus.

As shown in FIG. 1, the present apparatus has a gantry 100, a table 200 and an operator console 300. The gantry 100 scans a subject 10 carried by the table 200 by means of an X-ray radiation/detection device 110 to collect or acquire projection data of a plurality of views and inputs the same to the operator console 300.

The operator console 300 performs image reconstruction, based on the projection data inputted from the gantry 100 and displays a reconstructed image on a display 302. The image reconstruction is carried out by a dedicated computer lying within the operator console 300.

The operator console 300 sets a tube current of an X-ray tube. The X-ray tube current is set by the corresponding dedicated computer (X-ray tube current setting unit 301) lying within the operator console 300. Incidentally, the details of the setting of the X-ray tube current will be described later.

The operator console 300 also controls the operations of the gantry 100 and the table 200. Their control are performed by the dedicated computer lying within the operator console 300. The gantry 100 performs a scan on a predetermined scan condition under the control of the operator console 300, and the table 200 performs the positioning of the subject 10 such that a predetermined region is scanned.

The positioning thereof is conducted by adjusting the height of a table top 202 and the distance at which the cradle 204 is moved over the table top in the horizontal direction, by means of a built-in position adjustment mechanism.

An axial scan can be done by performing scanning in a state in which the cradle 204 has been stopped. A cine scan can be performed by carrying on the axial scan consecutively.

A helical scan can be conducted by continuously performing scans of plural times while the cradle 204 is being moved continuously. A cluster scan can be done by performing scans every stop position while the cradle 204 is being moved intermittently.

The adjustment to the height of the table top 202 is performed by swinging a support post 206 about its attached portion to a base 208. The table top 202 is displaced vertically and horizontally by swinging of the support post 206. The cradle 204 is moved over the table top 202 in the horizontal direction to cancel out the horizontal displacement of the table top 202. Scanning is done in a state in which the gantry 100 has been tilted, depending on scan conditions. The tilting of the gantry 100 is conducted by a built-in tilt mechanism.

Figure 2:
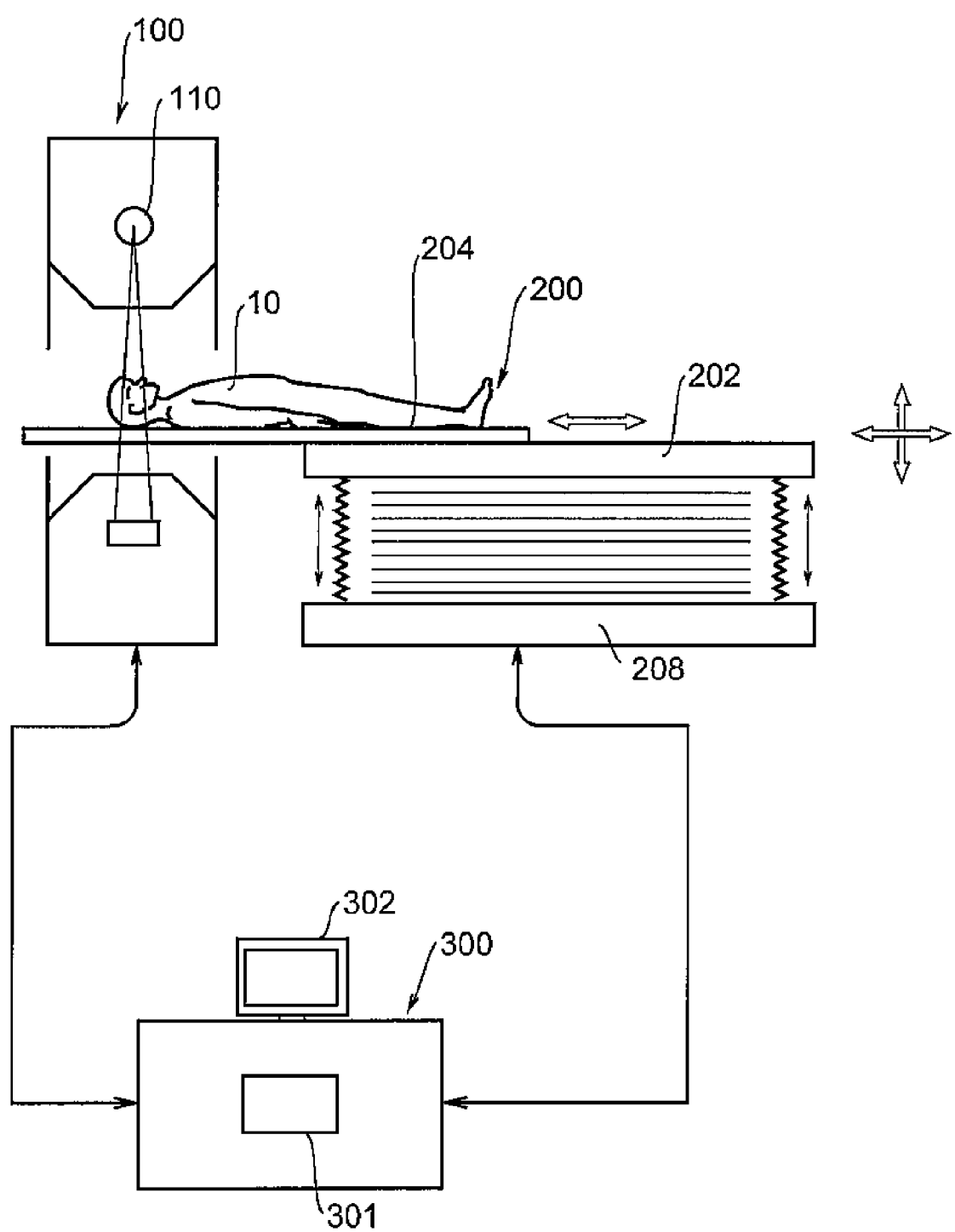
FIG. 2 is a diagram illustrating a construction of an X-ray CT apparatus which uses a tube current determining method corresponding to one example of a best mode for carrying out the invention.

Incidentally, the table 200 may be one based on a system in which the table top 202 moves up and down relative to the base 208 as shown in FIG. 2. The elevation of the table top 202 is conducted by a built-in elevating mechanism. The horizontal movement of the table top 202 with its elevation does not occur in the table 200.

Figure 3:
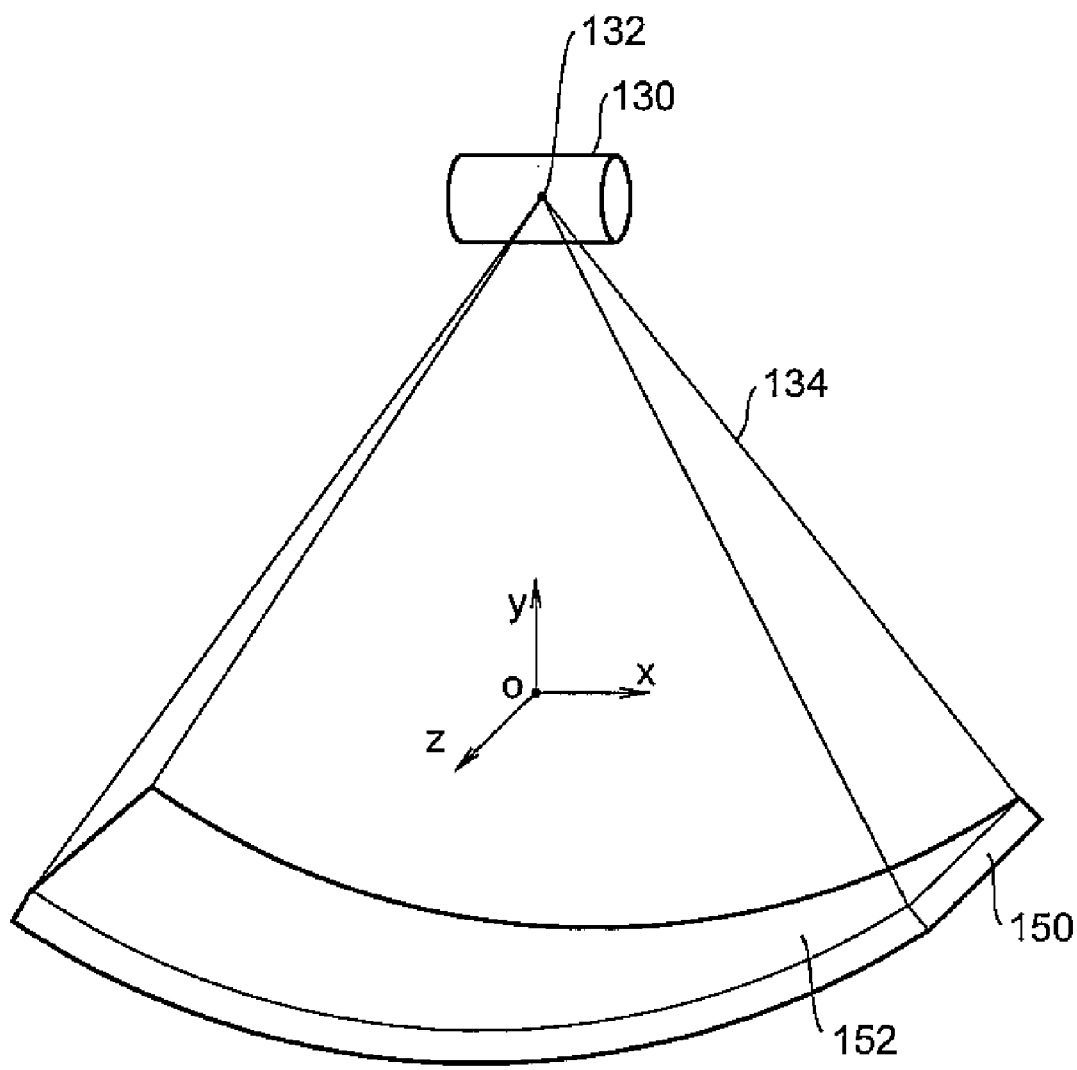
FIG. 3 is a diagram depicting a construction of an X-ray radiation/detection device.

A construction of the X-ray radiation/detection device 110 is typically shown in FIG. 3. The X-ray radiation/detection device 110 detects X rays 134 radiated from a focal point 132 of an X-ray tube 130 by using an X-ray detector 150.

The X rays 134 are formed by an unillustrated collimator and assume a cone beam or a fan beam X ray. A tube current of the X-ray tube 130 is controlled by the operator console 300.

The X-ray detector 150 has an X-ray incidence plane 152 which expands corresponding to the spread of the X rays on a two-dimensional basis. The X-ray incidence plane 152 is bent so as to constitute par of a cylinder. The central axis of the cylinder passes through the focal point 132.

The X-ray radiation/detection device 110 rotates about the center of photography or imaging, i.e., the central axis of an isocenter O. The central axis is parallel to the central axis of a partial cylinder formed by the X-ray detector 150.

Assume that the central-axial direction of rotation is taken as a z direction, the direction in which the isocenter O and the focal point 132 are connected is taken as a y direction and the direction orthogonal to the z and y directions is taken as an x direction. These x, y and z axes become three axes of a rotational coordinate system with the z axis as a central axis.

Figure 4:
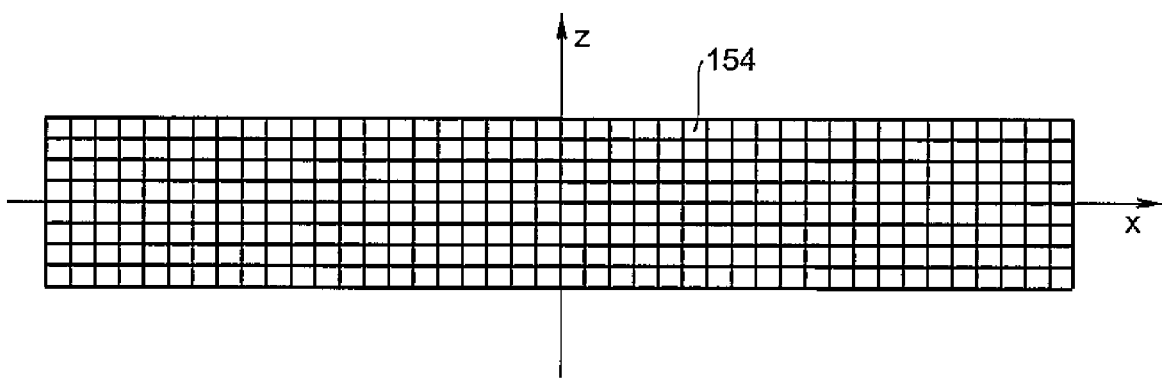
FIG. 4 is a diagram showing a construction of an X-ray incidence plane of an X-ray detector.

A plan view of the X-ray incidence plane 152 of the X-ray detector 150 is typically shown in FIG. 4. The X-ray incidence plane 152 includes detection cells 154 two-dimensionally arranged in the x and z directions. That is, the X-ray incidence plane 152 is configured as a two-dimensional array of the detection cells 154. Incidentally, when the fan beam X ray is used, the X-ray incidence plane 152 may be configured as a one-dimensional array of the detection cells 154.

Each individual detection cell 154 constitutes a detection channel of the X-ray detector 150. Thus, the X-ray detector 150 serves as a multi-channel X-ray detector. The detection cell 154 is constituted of a combination of a scintillator and a photo diode, for example.

Alternatively, the detection cell 154 is made up of a semiconductor having electrodes at both surfaces. For instance, CZT (Cadmium Zinc Telluride) is used as the semiconductor. Incidentally, the detection cell 154 is not limited to these and CdT (Cadmium Telluride) or HgI2 (Mercuric Iodide) may be used as the semiconductor. By using such a semiconductor, each photon can be converted to an electric signal efficiently.

A tube current determining procedure of the X-ray tube current setting unit 301 at the execution of cardiac imaging by the present apparatus will be explained using embodiments.

A first embodiment will explain an example for determining a tube current using a BMI. The tube current is given as a time product of currents and its unit is expressed in mAs. As a tube current determining criterion, an index related to image's noise is defined with respect to a reconstructed image. This index corresponds to an index specialized for cardiac imaging. This is hereafter called "Cardiac Image Noise Index: CINI"). It is also simply called "noise index CINI". The noise index CINI is given by a standard deviation or the like of each pixel value, for example.

The tube current is determined so as to assume such a current that an image having noise coincident with the corresponding noise index CINI can be photographed. Image noise to be noted corresponds to image noise at a central portion of an ascending main artery. The tube current is determined in such a manner that the image noise of this portion coincides with the noise index CINI.

The determination of the tube current is performed based on a predetermined relational expression. The relational expression is determined recursively from the past actual data of cardiac imaging. That is, a group in which image noise coincides with a desired noise index CINI is extracted from a number of cardiac images obtained by the past imaging, and a correlation between the constitution or body type of a patient and a tube current is determined. The desired noise index CINI is also called "desired noise index (DNI)" below. A body mass index (BMI) is used as an index for the body type of the patient. The BMI corresponds to a value obtained by dividing the weight expressed in kilogram by the square of the body height expressed in meter (m).

A correlation between the BMI and the tube current will be expressed in the following polynomial equation.

$$mAs = a0 + a1*BMI + a2*BMI^2 + a3*BMI^3 + \quad (1)$$

Coefficients ai (where i=1, 2, 3, . . . ) of respective terms in this polynomial equation are specified by fitting or the like.

When a plurality of desired noise indices DNI are defined, correlations between a BMI and a tube current are respectively determined with respect to the desired noise indices DNI. Thus, a generalized polynomial equation of BMI is obtained as follows:

$$mAs = b0(DNI) + b1(DNI)*BMI + b2(DNI)*BMI^2 + b3(DNI)*BMI^3 + \quad (2)$$

In the present polynomial equation, coefficients bi (DNI) become functions of desired noise index DNI.

Such a relational expression has been stored in a memory of the operator console 300. The operator console 300 determines a tube current using this relational expression upon cardiac imaging. That is, it calculates a body mass index BMI from the body height and weight of each patient inputted by an operator and plugs the BMI and a desired nose index DNI designated by the operator into the relational expression, thereby calculating a tube current.

The operator console 300 effects scaling corresponding to scan conditions such as a scan speed, a helical pitch, etc. on the calculated value of tube current to determine a tube current adapted to the scan conditions and performs cardiac imaging using the tube current.

An image photographed or imaged under this tube current becomes constant in image noise even with respect to any body shape in patient. It is therefore possible to stabilize the quality of each image and perform diagnosing interpretation of X rays easily and accurately.

A second embodiment will explain an example in which a tube current is determined based on the result of noise measurement at preliminary imaging. When coronary angiographic imaging is conducted, preliminary imaging using a small amount of contrast agent is carried out before actual imaging to examine timing or the like for contrast achievement. In such a case, the tube current may be determined using the result of preliminary imaging.

Determining the tube current utilizing the result of preliminary imaging is conducted using the following equation.

$$mAs(c) = k(pitch)*(Nb/Nc)^2*(T(b)/T(c))*mAs(b) \quad (3)$$

wherein Nb: noise of image obtained by preliminary imaging, Tb: slice thickness at preliminary imaging, and mAs(b): tube current at preliminary imaging. Further, Nc indicates a desired noise index of an image obtained by the actual imaging, Tc indicates a slice thickness at the actual imaging, and mAs(c) indicates a tube current at the actual imaging. k(pitch) indicates a scan mode coefficient and is used to perform conversion between preliminary imaging conducted in a cine scan and the actual imaging conducted in a helical scan. Incidentally, the noise of the image is noise in a state in which the concentration of a contrast agent has reached the peak.

As expressed in the present equation, the tube current mAs (c) at the actual imaging is determined by multiplying the tube current mAs(b) at the preliminary imaging by the scan mode coefficient k(pitch), the square of the ratio between a measured value Nb of the noise of the image obtained by the preliminary imaging and an index Nc related to the noise of the image obtained by the actual imaging, and the ratio between the slice thickness Tb at the preliminary imaging and the slice thickness Tc at the actual imaging.

The image photographed or imaged under such a tube current becomes constant in image noise even with respect to any patient of body shape. It is therefore possible to stabilize the quality of each image and perform diagnosing interpretation of X rays easily and accurately.

What is claimed is:

1. An X-ray CT apparatus comprising:
   an X-ray radiation/detection device comprising an X-ray tube configured to apply X-rays and an X-ray detector configured to detect the X-rays applied by said X-ray tube; and
   an X-ray tube current setting unit configured to set an X-ray tube current based on an index related to image noise and a BMI of a subject.

2. The X-ray CT apparatus according to claim 1, wherein said X-ray tube current setting unit is configured to set the X-ray tube current at imaging of a heart of the subject.

3. The X-ray CT apparatus according to claim 2, wherein the image noise is at a central portion of an ascending main artery.

4. The X-ray CT apparatus according to claim 1, wherein the X-ray tube current is calculated using a function with the BMI as a variable.

5. The X-ray CT apparatus according to claim 4, wherein the function is given as a polynomial equation of the BMI.

6. The X-ray CT apparatus according to claim 5, wherein each coefficient of the polynomial equation is a function of the index.

7. An X-ray CT apparatus comprising:
   an X-ray radiation/detection device comprising an X-ray configured to apply X-rays and an X-ray detector configured to detect the X-rays applied by said X-ray tube;
   a noise measuring unit configured to measure image noise obtained by preliminary imaging of a subject, the preliminary imaging conducted ahead of actual imaging of the subject; and
   an X-ray tube current setting unit configured to set an X-ray tube current at the actual imaging, the X-ray tube current determined based on both an X-ray tube current at the preliminary imaging and a ratio between a measured value of noise at the preliminary imaging and an index related to image noise.

8. The X-ray CT apparatus according to claim 7, wherein said X-ray tube current setting unit is configured to set the X-ray tube current at imaging of a heart of the subject.

9. The X-ray CT apparatus according to claim 8, wherein said X-ray tube current setting unit is configured to set the X-ray tube current at execution of angiographic imaging of the heart of the subject.

10. The X-ray CT apparatus according to claim 8, wherein the image noise is at a central portion of an ascending main artery.

11. A method for setting an X-ray tube current of an X-ray CT apparatus, said method comprising:
    determining an X-ray tube current based on an index related to image noise and a BMI of a subject; and
    setting the X-ray tube current for use during imaging of the subject.

12. The method according to claim 11, wherein setting the X-ray tube current comprises setting the X-ray tube current at imaging of a heart of the subject.

13. The method according to claim 12, wherein the noise is at a central portion of an ascending main artery.

14. The method according to claim 11, wherein determining an X-ray tube current comprises calculating the X-ray tube current using a function with the BMI as a variable.

15. The method according to claim 14, wherein the function is given as a polynomial equation of the BMI.

16. The method according to claim 15, wherein each coefficient of the polynomial equation is a function of the index.

17. A method for setting an X-ray tube current of an X-ray CT apparatus, said method comprising:
    measuring image noise obtained by preliminary imaging of a subject, the preliminary imaging conducted ahead of actual imaging of the subject; and
    setting an X-ray tube current at the actual imaging, the X-ray tube current based on both an X-ray tube current at the preliminary imaging and a ratio between a measured value of noise at the preliminary imaging and an index related to image noise.

18. The method according to claim 17, further comprising setting the X-ray tube current at imaging of a heart of the subject.

19. The method according to claim 18, further comprising setting the X-ray tube current at execution of angiographic imaging of the heart of the subject.

20. The method according to claim 18, wherein the image noise is at a central portion of an ascending main artery.

* * * * *